(12) United States Patent
Hollander et al.

(10) Patent No.: US 6,406,296 B1
(45) Date of Patent: Jun. 18, 2002

(54) IMPLANT WITH ENLARGED PROXIMAL SEGMENT

(75) Inventors: Bruce Hollander; Ingo Kozak, both of Deerfield Beach, FL (US)

(73) Assignee: Bio-Lok International, Inc., Deerfield Beach, FL (US)

(*) Notice: Subject to any disclaimer, the term of this patent is extended or adjusted under 35 U.S.C. 154(b) by 0 days.

(21) Appl. No.: 09/714,201

(22) Filed: Nov. 17, 2000

Related U.S. Application Data

(63) Continuation-in-part of application No. 09/476,882, filed on Jan. 4, 2000, and a continuation-in-part of application No. 09/312,114, filed on Jan. 4, 1999, now Pat. No. 6,149,432, which is a continuation-in-part of application No. 08/172,702, filed on Dec. 27, 1993, now Pat. No. 5,964,766.

(51) Int. Cl.[7] ............................................. A61C 8/00
(52) U.S. Cl. ....................................................... 433/174
(58) Field of Search ................................. 433/173, 174

(56) References Cited

U.S. PATENT DOCUMENTS

| | | | | |
|---|---|---|---|---|
| 4,406,623 A | * | 9/1983 | Grafelmann et al. | 433/174 |
| 5,259,398 A | * | 11/1993 | Vrespa | 433/174 X |
| 5,435,723 A | * | 7/1995 | O'Brien | 433/174 |
| 5,816,812 A | * | 10/1998 | Kownacki et al. | 433/174 |

* cited by examiner

*Primary Examiner*—Nicholas D. Lucchesi
(74) *Attorney, Agent, or Firm*—M. K. Silverman

(57) ABSTRACT

A dental implant for securement within a bore within a maxilla or mandible, inclusive of the cortical bone includes a threaded elongate anchor having a proximal upper portion having a larger outside diameter than that of an integral distal lower portion, the anchor defining, in axial cross-section, an envelope in which the upper portion substantially defines a cylinder and the lower portion substantially defines a conical section, and an engagable head integrally dependent from a proximal surface of the proximal portion of the anchor, the head having an outside diameter smaller than a greatest outside diameter of the proximal portion of the anchor, the outside diameter of the head also equal or less than a diameter of an entry region into the bore. A greatest axial length of the lower portion defines a length of about 6.0 mm.

19 Claims, 4 Drawing Sheets

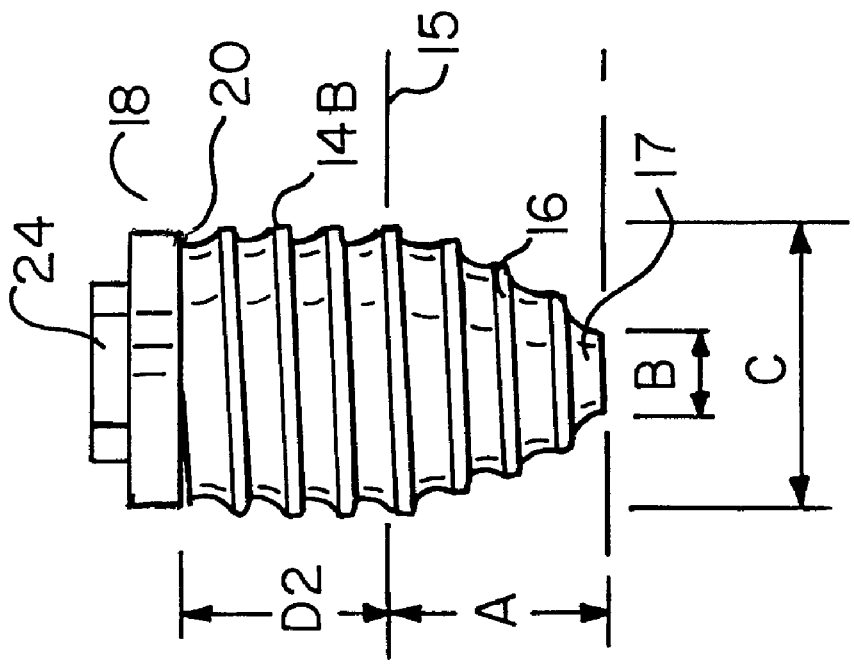
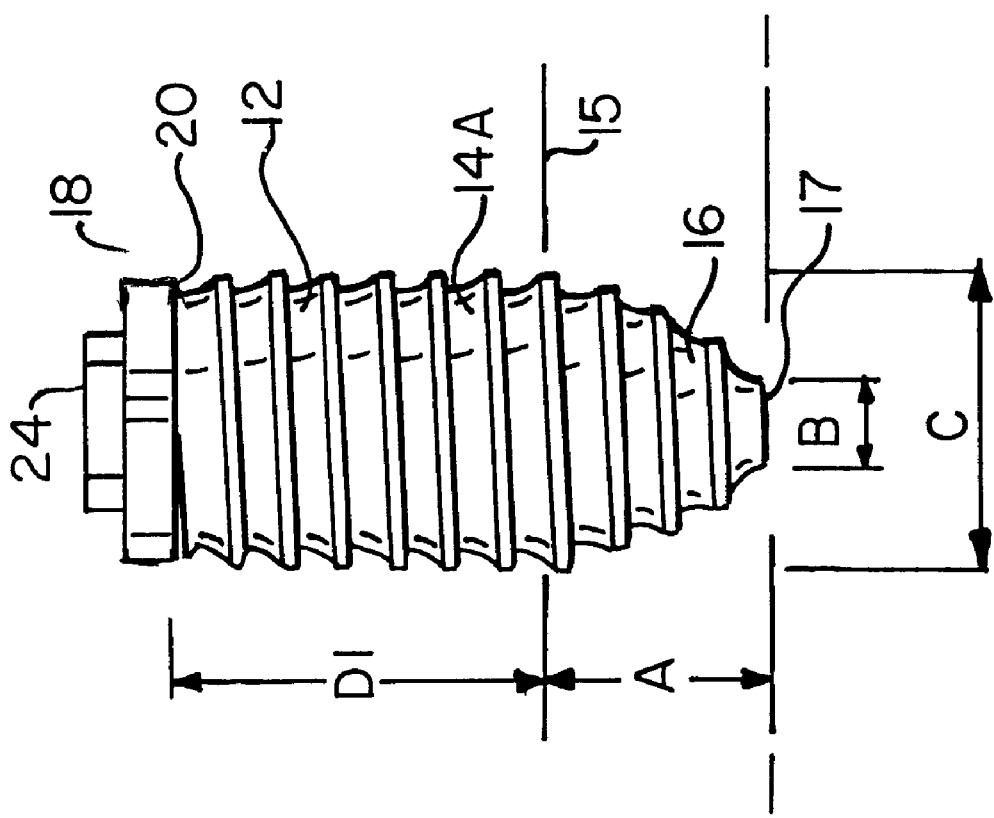

IMPLANT WITH ENLARGED PROXIMAL SEGMENT

REFERENCE TO RELATED APPLICATIONS

This case is a continuation-in-part of both application Ser. No. 09/312,114, filed Jan. 4, 1999, now U.S. Pat. No. 6,149,432 entitled Buttress Thread Dental Implant; and of application Ser. No. 09/476,882, filed Jan. 4, 2000, now abandoned, entitled Dental Implant with Enlarged Proximal Segment application Ser. No. 09/312,114 is a continuation-in-part of application Ser. No. 08/172,702, filed Dec. 27, 1993, now U.S. Pat. No. 5,964,766.

BACKGROUND OF THE INVENTION

The present invention relates to an improvement in dental implants including, without limitation, dental implants of the type taught in U.S. Pat. No. 5,964,766 (1999) entitled Buttress Thread Implant.

A historic concern in the technology of dental implantation has been that of maximizing securement, more technically known as bio-integration, of the dental implant within the cortical bone of the maxilla or mandible of the dental patient. Many structures and methods have been suggested to achieve this end, the same including, without limitation, buttress thread implants of the type referenced above.

The present invention therefore relates to a novel structure for a dental implant, the design for use with a specific method for the provision of enhanced bone-to-implant securement. As such, the instant invention responds to a long-felt in the art of implant dentistry.

SUMMARY OF THE INVENTION

A dental implant for securement within a bore within a maxilla or mandible, inclusive of the cortical bone thereof, includes a threaded elongate anchor having a proximal upper portion having a larger outside diameter than that of an integral distal lower portion thereof, said anchor defining, in axial cross-section, an envelope in which said upper portion substantially defines a cylinder and said lower portion substantially defines a conical section, and an engagable head integrally dependent from a proximal surface of said proximal portion of said anchor, said head having an outside diameter smaller than a greatest outside diameter of said proximal portion of said anchor, said outside diameter of said head also equal or less than a diameter of an entry region into said bore. A greatest axial length of said lower portion comprises a length of about 6.0 mm.

It is an object of the invention to provide a dental implant typically having a threaded lateral surface thereof, the implant having superior characteristics of gripping to the mandible or maxilla bone interface and of resistance to micro-mechanical movements such as stresses and the like.

It is another object to provide an improved dental implant, and method of use thereof, having improved characteristics of axial and rotational stability relative to the anatomical bone interface.

It is a further object of the invention to provide an improved dental implant which, in combination with a specially sized bone bore provides for enhanced stability and durability relative to prior art structures and methods.

The above and yet other objects and advantages of the present invention will become apparent from the hereinafter set forth Brief Description of the Drawings, Detailed Description of the Invention and Claims, appended herewith.

BRIEF DESCRIPTION OF THE DRAWINGS

FIGS. 1A and 1B are views showing variations in the D1 and D2 dimension of the upper cylindrical portion of the anchor of the present implant.

DETAILED DESCRIPTION OF THE INVENTION

Figure 1:
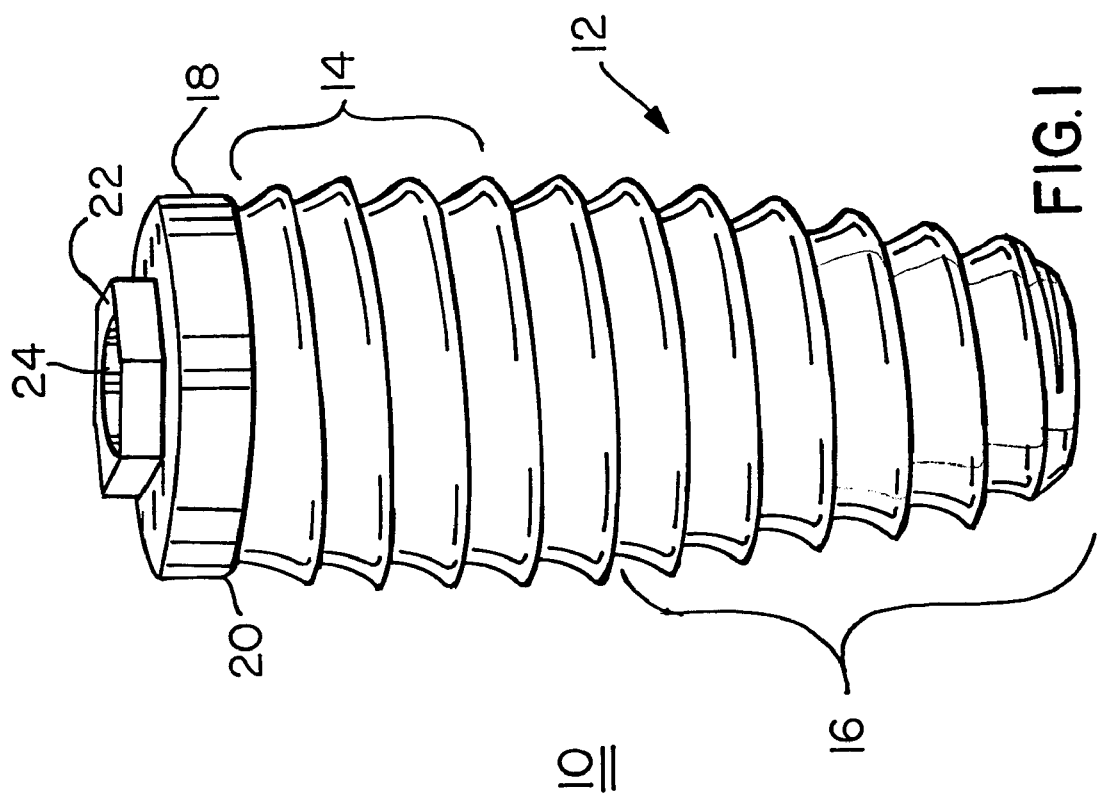
FIG. 1 is an elevational view showing the surface of a dental implant in accordance with the present invention.

With reference to the elevational view of FIG. 1, a dental implant 10 may be seen to include a rigid anchor 12 preferably including threading upon lateral surfaces thereof. Such threading may include, without limitation, buttress threading and machine screw threading.

Said anchor includes proximal and distal portions 14 and 16 respectively wherein the greatest outside diameter of the proximal segment is greater than the greatest outside diameter of the distal segment. In a preferred embodiment, thermal axial length of the proximal segment is about one-third of the total length of the implant. The dental implant further includes an engagable head 18 which is integrally dependent from a proximal surface 20 of said proximal portion 14 of the implant anchor 12. It is noted that the outside diameter of said head 18 is smaller than the greatest outside diameter of said proximal portion 14 as, more particularly, may be noted with reference to the top axial plan view of FIG. 2. Therein, it is noted that the outside diameter of said head 18 is between about 0.25 to 0.60 millimeters smaller than the greatest outside diameter of said proximal segment 14 of the anchor 12.

It is further noted that head 18 includes an engagable grippable portion 22, typically configured for engagement by a hex-head torque wrench.

Figure 2:
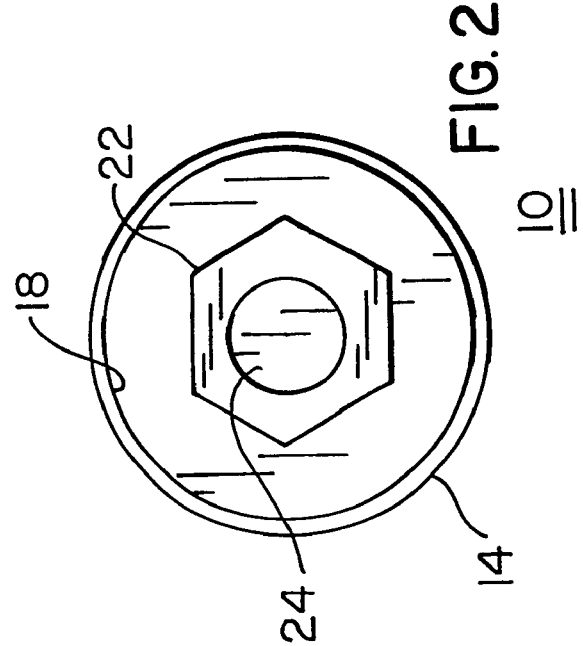
FIG. 2 is a top plan view of the implant of FIG. 1.

As may be further noted in FIGS. 1 and 2, the head and anchor include an axial longitudinal bore 24 within which an elongate element of an abutment, or a screw-anchoring abutment ultimately to be secured within implant 10, is placed.

In the views of FIGS. 1A and 1B, it is shown that said cylindrical proximal portion 14 of the implant anchor 12 may be provided in a range of axial lengths as is indicated by the dimensions D1, corresponding to proximal portion 14a, in FIG. 1A, and dimension D2 in FIG. 1B corresponding to proximal portion 14b therein. The range of dimension D will typically fall between 2 and 9 millimeters, whereas the length A of distal conical segment 16 will always be that of approximately 6 millimeters, with a possible range of 4.8 to 7.2 millimeters. It has, more particularly, been determined that an axial length of about 6 millimeters of said conical distal portion 16 is most ergonomic and has been found, in combination with the particular shape of the conical distal portion 16 and geometry of bore 26 (which is complemental to that of segment 16) optimizes biointegration of anchor 12 within the osseotomy site. See FIGS. 3 and 6. Other important dimensions of distal portion 16 are that of dimension C which is that of the diameter of the anchor at a transition plane 15 at which proximal portion 14 begins to taper into distal portion 16. This dimension has been found to optimally fall within a range of 4 to 7 millimeters, while dimension A (as above noted) remains fixed at approximately 6 millimeters. Dimension B, that is, a flat planar distal-most surface of distal segment 16 will typically fall in a range of 1 to 3 millimeters.

Figure 3:
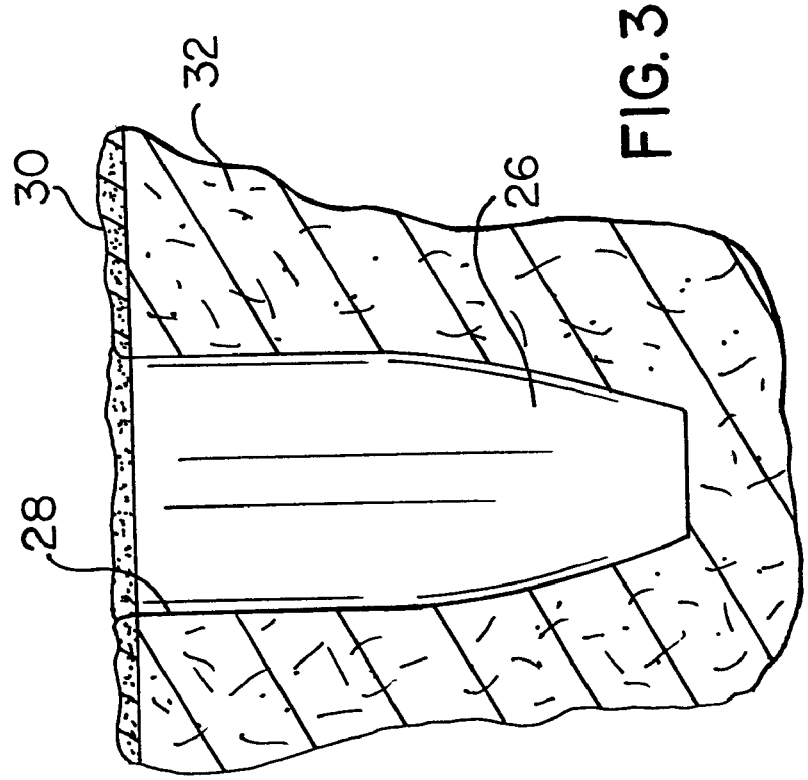
FIG. 3 is a vertical schematic view through the axis of rotation of a bone bore formed in accordance with the inventive method.

With reference to the schematic view of FIG. 3, there is shown a bore 26, which has been drilled within a cortical bone 32 of a maxilla or mandible of a patient for placement of an implant. Above the cortical bone is shown soft tissue of gum 30. Within bore 26 is an entry region 28 which may exhibit a diameter typically greater than a distal region of said bore, however, of a diameter generally equal to the outside diameter of said implant head 18, as is more fully described below.

Figure 4:
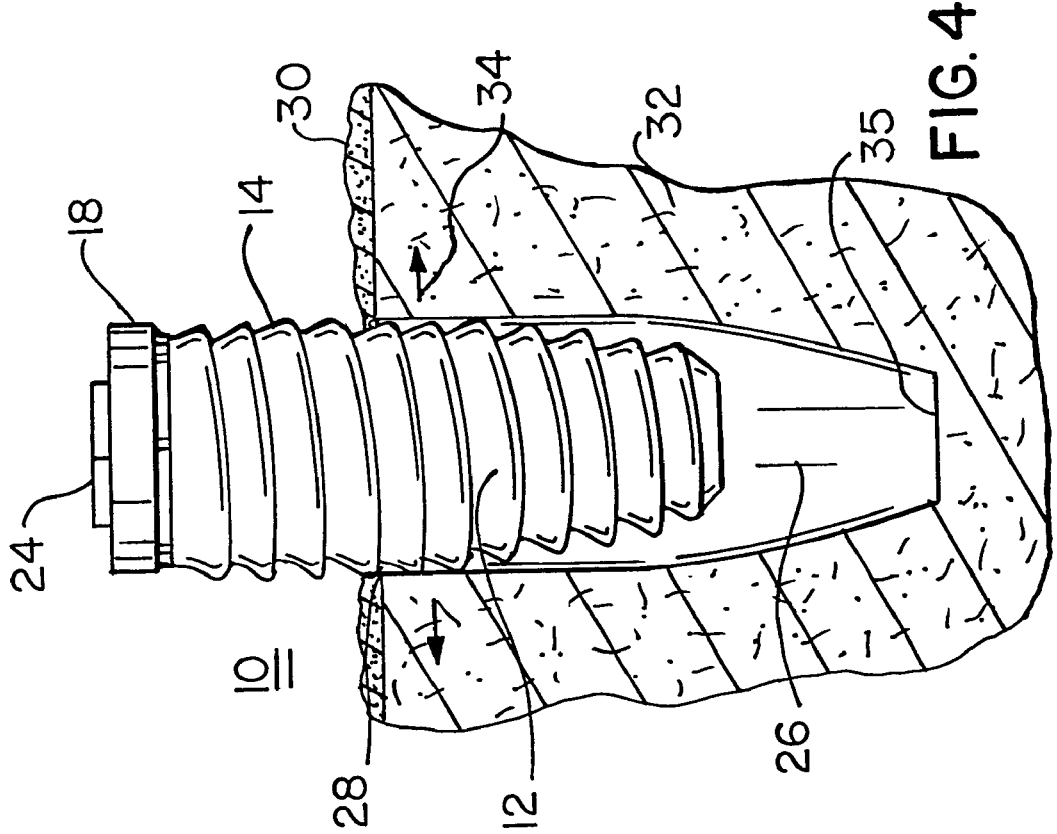
FIG. 4 is a schematic view, sequential to the view of FIG. 3, showing initial insertion of the implant into the bone bore.
Figure 5:
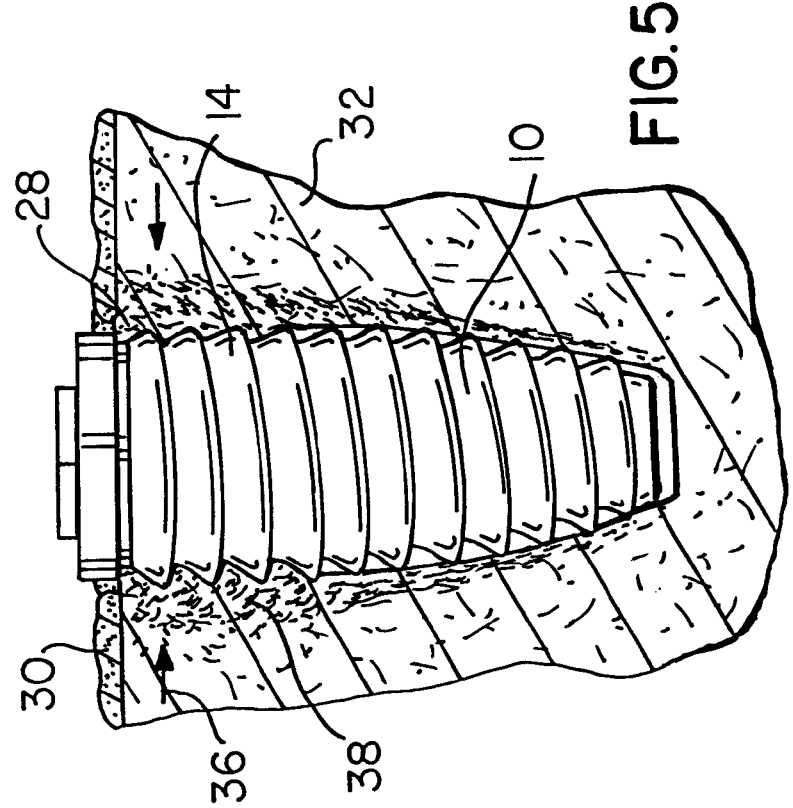
FIG. 5 is a schematic view, further sequential to the view of FIG. 4, showing a substantially complete insertion of the implant into the bone bore.

With reference to FIG. 4, there is shown a rotational entry of the implant 10 into bone bore 26 at the area of transition between the distal portion 16 and proximal portion 14 of the implant anchor 12. At this point, because of the enhanced diameter of a proximal segment relative to the diameter of entry region 28 of the bore 26, bone 32 is compressed radially outwardly as is depicted by arrows 34 in FIG. 4. Accordingly, during the insertion interval starting at the time of the view of FIG. 4 and continuing until the time just before the view of FIG. 5, cortical bone 32 is forced radially outwardly to accommodate the greater outside diameter of proximal implant portion 14. However, by the time that the point of the procedure which is shown in FIG. 5 is reached, bone 32 will compress about proximal portion 14 as in indicated by radially inwardly directed arrows 36 and the darkened region 38 in FIG. 5. Also, proximal segment 14 will cut into bone 32 as the segment is advanced into bone 26.

Figure 6:
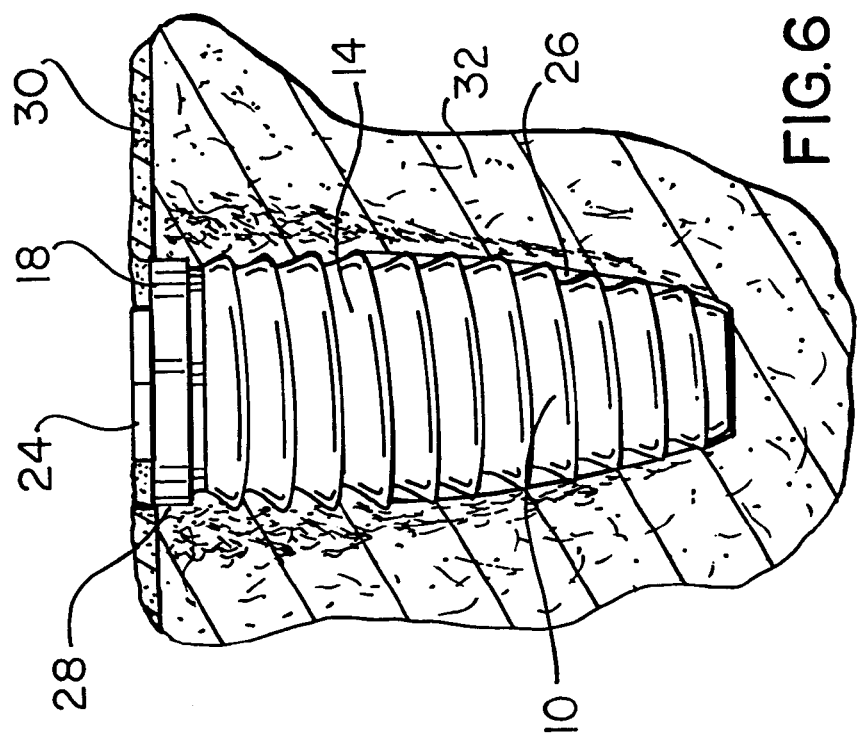
FIG. 6 is a schematic view, sequential to the view of FIG. 5, showing completion of the insertion of the implant into the bone bore.

This bone-to-implant engagement process is further shown in FIG. 6 in which, as may be noted, head 18 of the implant 10 has been advanced within bore 26, beneath the gum line 30 such that the head 18 is press-fittably engaged by the soft tissue of the gum. Accordingly, as is depicted, after completion of the method of the present invention, proximal segment 14 of the implant is compressible engaged by bone 32, as is head 18 by soft tissue 30. As such, an improved bone-to-implant securement, with improved osseointegration of the implant to the bone, is effected.

Where the anchor is provided with a buttress threading, such threading is axially symmetric and exhibits (1) radially circumferential spiral pitch surfaces, in a range of about 22 to about 28 pitch surfaces per axial inch, (2) an upper concave bevel surface above each pitch surface, which is longer than a lower bevel surface beneath each pitch surface, and (3) an intersection of each plane of each pitch surface with each plane of each lower bevel surface defining a total included angle in a range of about 90 to about 130 degrees, said anchor having minor thread diameters at intersections, between pitch surfaces, of said upper and lower bevel surfaces, said pitch surfaces and said minor thread diameters defining, at any axial radius of said rigid body, a ratio of thread pitch to thread depth in a range of about 1.25:1 to about 1.40:1. Each of said lower bevel surfaces define a total included angle in a range of about 20 to about 30 degrees relative to any given axial radius of said implant at a minor thread diameter thereof.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

Having thus described our invention, what we claim as new, useful and non-obvious and, accordingly, secured by Letters Patent of the United States is:

1. A dental implant for securement within an entry region of a bore, having a given diameter, within a maxilla or mandible, inclusive of the cortical bone thereof, said implant comprising:
   (a) a constant-pitched threaded elongate bone-engaging anchor having a proximal upper portion having an outside diameter larger than that of an integral distal lower portion thereof, said larger diameter also larger than said given diameter of said entry region of said bore, said anchor defining, in axial cross-section, an envelope in which said upper portion substantially defines a cylinder and said lower portion substantially defines a conical section; and
   (b) an engagable head integrally dependent from a proximal surface of said proximal portion of said anchor, said head having an outside diameter smaller than said outside diameter of said proximal portion of said anchor, said outside diameter of said head also substantially equal to said given diameter of said entry region of said bore.

2. The implant as recited in claim 1, in which a greatest axial length of said lower portion comprises a length in a range of about 4.8 to about 7.2 mm.

3. The implant as recited in claim 2, in which said greatest axial length comprises about 6.0 mm.

4. The implant as recited in claim 2, in which an axial length of said upper portion comprises a dimension in a range of between about 2 mm to about 9 mm.

5. The implant as recited in claim 4, in which a mean diameter of said anchor, at a plane of transition from said upper to lower portions thereof comprises a dimension in a range of about 4 mm to about 7 mm.

6. The implant as recited in claim 5, in which a distal-most end of said lower portion defines a substantially flat radial surface having a diameter in a range of about 1 mm to about 3 mm.

7. The implant as recited in claim 1 in which said diameter of said head is between about 0.25 to about 0.6 mm smaller than a greatest diameter of said anchor.

8. The implant as recited in claim 2, in which said threaded anchor comprises a buttress threading upon a lateral surface thereof.

9. The implant as recited in claim 8 in which said anchor comprises:
   a rigid body having thereupon axially symmetric and radially circumferential spiral pitch surfaces, in a range of about 22 to about 28 pitch surfaces per axial inch, an upper concave bevel surface above each pitch surface, which is longer than a lower bevel surface beneath each pitch surface, and an intersection of each plane of each pitch surface and each plane of each lower bevel surface defining a total included angle in a range of about 90 to about 130 degrees, said rigid body having minor thread diameters at intersections, between pitch surfaces, of said upper and lower bevel surfaces, said pitch surfaces and said minor thread diameters defining, at any axial radius of said rigid body, a ratio of thread pitch to thread depth in a range of about 1.25:1 to about 1.40:1.

10. The implant as recited in claim 9 in which each of said lower bevel surfaces define a total included angle in a range of about 20 to about 30 degrees relative to any given axial radius cross-section of said implant at a minor thread diameter thereof.

11. The implant as recited in claim 10, in which said lower bevel surfaces a comprise substantially flat surfaces.

12. The implant as recited in claim 10, in which said concave upper bevel surfaces of said pitch surfaces each define a radius in a range of about 0.040 inches.

13. The implant as recited in claim 11, in which said pitch surface comprise, at any axial radius, of said rigid body, a ratio of major thread diameter to said minor thread diameter in a range of about 1.2:1 to about 1.3:1.

14. The implant as recited in claim 13, in which the difference between said major and minor thread diameters, at a given axial radius comprises about 0.030 inches.

15. The implant as recited in claim 10, in which a ratio of thread pitch to thread depth is, at any axial radius, in a range of about 1.25:1 to about 1.40:1.

16. The implant as recited in claim 10, in which said total included angle comprises about 110 degrees.

17. The implant as recited in claim 10, in which a length of said upper bevel surface comprises about twice the length of said lower bevel, at any axial radius of said rigid body.

18. The implant as recited in claim 10, in which a ratio of diameters of a major base to a lower base of said conical section is characterized by a ratio in a range of 1.5:1 to 4:1.

19. The implant as recited in claim 2, in which said threaded anchor comprises machine screw threading upon a lateral surface thereof.

* * * * *